(12) United States Patent
Thompson et al.

(10) Patent No.: US 7,119,338 B2
(45) Date of Patent: Oct. 10, 2006

(54) TRANSLATABLE ULTRASONIC THERMOGRAPHY INSPECTION APPARATUS AND METHOD

(75) Inventors: Jeffrey G. Thompson, Kent, WA (US); Clyde T. Uyehara, Kent, WA (US)

(73) Assignee: The Boeing Company, Chicago, IL (US)

( * ) Notice: Subject to any disclaimer, the term of this patent is extended or adjusted under 35 U.S.C. 154(b) by 288 days.

(21) Appl. No.: 10/776,623

(22) Filed: Feb. 12, 2004

(65) Prior Publication Data

US 2004/0159790 A1 Aug. 19, 2004

Related U.S. Application Data

(63) Continuation-in-part of application No. 10/324,014, filed on Dec. 20, 2002.

(51) Int. Cl.
  *G01J 5/02* (2006.01)
(52) U.S. Cl. .................................... 250/341.6
(58) Field of Classification Search ............ 250/341.6
  See application file for complete search history.

(56) References Cited

U.S. PATENT DOCUMENTS 4,304,133 A * 12/1981 Feamster, III ................ 73/633
5,634,378 A * 6/1997 Burkhardt et al. ...... 74/501.5 R
6,838,670 B1 * 1/2005 Lewis et al. ............. 250/341.6

FOREIGN PATENT DOCUMENTS

DE   4221486 A1 * 2/1993

* cited by examiner

*Primary Examiner*—David Porta
*Assistant Examiner*—Christopher Webb
(74) *Attorney, Agent, or Firm*—Baker & Hostetler LLP

(57) ABSTRACT

A portable thermal imaging apparatus uses an ultrasonic acoustical source and an infrared camera to examine a flat or curved specimen such as the surface of the fuselage of an aircraft for defects such as subsurface disbonds, delaminations, cracks, corrosion, embedded contaminants, inclusions, and voids. The apparatus includes a base framework removably attachable to the specimen by a set of vacuum cups and a pair of guide rails along which the imaging apparatus can travel to allow multiple images to be captured without relocating the apparatus on the specimen. The acoustical signal from the ultrasonic source sweeps over a range of frequencies in order to excite defects of greatly differing size to exhibit local heating.

31 Claims, 5 Drawing Sheets

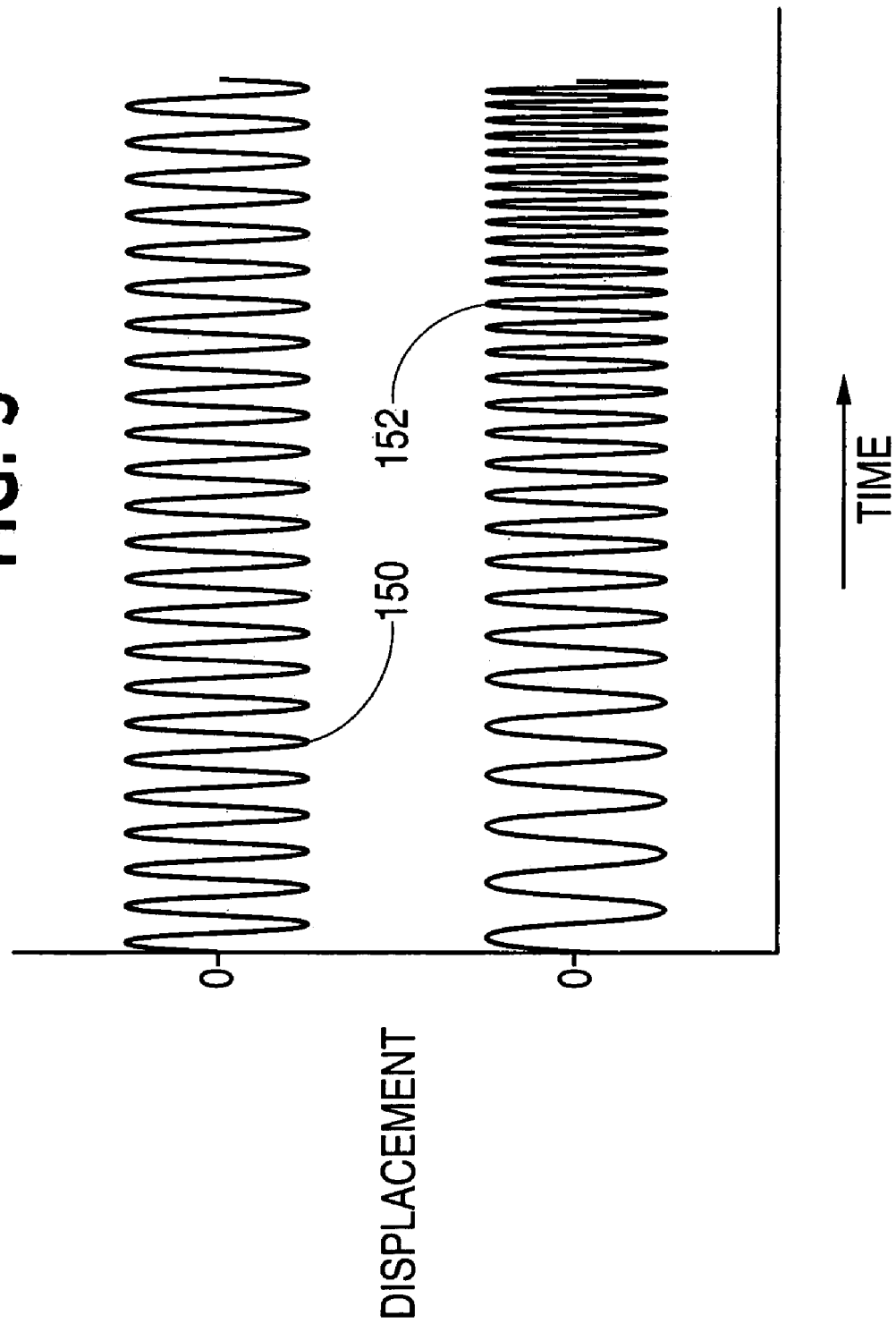

TRANSLATABLE ULTRASONIC THERMOGRAPHY INSPECTION APPARATUS AND METHOD

CLAIM FOR PRIORITY

This application is a continuation-in-part of, and Applicants hereby claim the benefit of the filing date of, U.S. patent application Ser. No. 10/324,014, Ultrasonic Thermography Inspection Method and Apparatus, filed Dec. 20, 2002, the disclosure of which is incorporated herein in its entirety by reference.

FIELD OF THE INVENTION

The present invention relates to the use of ultrasonic thermography for inspecting the structural integrity of certain components, materials and/or structures. More particularly, the present invention relates to an apparatus and method for positioning an ultrasonic thermography test apparatus to ease and speed field inspections of aircraft fuselages and other structural components.

BACKGROUND OF THE INVENTION

Establishing and verifying the structural integrity of components and structures is important in many industries, such as aviation, automobiles, petroleum, and construction. Loss of structural integrity can be caused by material defects, such as disbonds, delaminations, cracks, corrosion, embedded contaminants, inclusions, and voids that can exist in a composite or monolithic component or structure. For example, it is important in the aviation industry that reliable nondestructive inspection (NDI) techniques exist to examine the structural integrity of each aircraft's fuselage and other structural components to assure that the aircraft will not experience structural failure during operation. Point-by-point inspection of airplanes may thus be advisable, and may be required to be performed, at routine service intervals. Similarly, by way of example, non-invasive inspection and analysis of automotive components such as load-bearing panels, and of petroleum and other chemical transport pipelines, can be of value in the detection of minor flaws, allowing them to be repaired and preventing them from growing into potentially harmful ruptures.

One current method for non-invasive analysis of materials and/or components for defects includes treating the material or component with a dye penetrant such that the dye enters any crack or defect that may exist. The component is then cleaned and then treated with a powder that causes the dye remaining in the defects to wick into powder. Next, ultraviolet light is applied to the material or component causing the residual dye remaining in any cracks or defects to fluoresce. This technique has drawbacks however. The dye sometimes is not suitable to identify cracks that located in areas other than the surface of the component. In addition, this technique is can be operator dependent in that the person performing this technique should be adequately trained and skilled.

Other methods currently utilized for the non-invasive analysis and inspection of materials and components include use of an electromagnetic current and use of thermal imaging including ultrasonic excitation or ultrasonic thermography.

The non-invasive analysis method of using an electromagnetic current is carried out by employing an electromagnetic coil to induce eddy currents in the test material or component. The current pattern changes at the location of a defect or crack. This technique requires point by point inspection, which can be labor intensive and is to some extent limited to only specific types of defects. In addition, the evaluator must be properly trained and skilled.

Ultrasonic thermography is a non-invasive analysis method by which a component, material, or structure, or a portion thereof, is excited with an ultrasonic pulse using an ultrasonic transducer pressed against the surface of the test subject. The resulting mechanical vibration of the subject under test tends to feature differential motion across the face of any defects that may be present, producing friction and causing the defects to heat up sharply, while defect-free areas of the test subject tend to be only minimally and uniformly heated by the vibration. Heat diffusing to the surface from a defect within the volume of a test subject causes a transient local surface temperature increase that can be detected as a bright spot in an image captured shortly after the ultrasonic pulse using, for example, an infrared camera. This ultrasonic thermography technique can identify disbonds, delaminations, cracks, corrosion, embedded contaminants, inclusions, voids, and other types of defects within a broad range of metallic, fiber reinforced plastic, composite, and other structural materials used in the transportation, construction, and other manufacturing industries. It is to be understood that finding defects is not the same as correcting them; ultrasonic thermography as applied herein is primarily a tool for detection.

Ultrasonic thermography has proven successful for detecting defects in materials and components in research, production, and operational maintenance environments. Some presently available analysis systems employing ultrasonic thermography techniques have drawbacks and limitations, however. For example, some presently available ultrasonic thermography systems can analyze only small specimens, and are generally restricted to laboratory use. Some other such systems require manual placement, orientation, and application of force between the transducer and the test surface, which requirements can degrade the repeatability, accuracy, and noninvasive nature of the technique. That is, too much or too little pressure applied to the transducer during a pulse may degrade the repeatability of detection, while misalignment of the transducer can cause the part or surface being inspected to be cut or burned, or can cause damage to surface finishes. Such systems are thus not always well suited for field inspection of materials or components, or for inspection of large objects, such as fuselages and flight control structures of in-service airplanes.

Accordingly, it is desirable to provide an apparatus and method for detecting defects of multiple types in both metal and composite structures. It is also desirable to provide an apparatus and method for effectuating the quick and efficient inspection and analysis of large components and/or large amounts of materials, such as entire airplane fuselages and structures, in real time. It is further desirable to provide a repeatable analysis apparatus and method using ultrasonic thermography to effectuate inspection of large components or areas to detect disbonds, delaminations, cracks, corrosion, embedded contaminants, inclusions, voids, and other defect types. It is desirable as well that an ultrasonic thermography apparatus should be readily transportable, usable under field as well as laboratory conditions, and usable by a small team of operators.

SUMMARY OF THE INVENTION

The foregoing needs are met, at least in part, by the present invention, where, in one aspect, a portable thermal imaging analysis apparatus for analyzing a specimen having a surface comprises a base framework that removably attaches to the specimen, a frame that slideably attaches to the base framework, a sound source that mounts to the frame and couples its energy to the specimen, a thermal imaging camera directed toward the specimen, and a controller connected to the sound source and the thermal imaging camera.

In accordance with another aspect of the present invention, a portable thermal imaging analysis apparatus for analyzing a specimen having a surface comprises means for attaching a thermal imaging analysis apparatus to a specimen, means for moving a thermal imaging analysis apparatus across a region of a specimen, means for generating an acoustic signal with energy content along a motional axis perpendicular to a surface of a specimen, means for detecting thermal response to stimulation by the generating means, and means for controlling the generating means and the detecting means.

In accordance with yet another aspect of the present invention, a method for portable thermal imaging analysis of a specimen having a surface comprises the steps of attaching a thermal imaging apparatus to a specimen, repositioning a thermal imaging apparatus at a multiplicity of sites across a region of a specimen, generating an acoustical signal with energy content along a motional axis generally perpendicular to the surface of the specimen, detecting thermal response to stimulation by the acoustical signal, and controlling the acoustical signal generation and image detection operations.

In accordance with still another aspect of the present invention, a portable thermal imaging analysis apparatus for analyzing a specimen having a surface comprises a base framework that removably attaches to the specimen, a sound source that mounts to the frame and couples acoustical energy into the specimen, wherein the acoustical energy is characterized by a principal frequency that changes with time, a thermal imaging camera that captures infrared images of the specimen, and a controller connected to the sound source and the thermal imaging camera.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 5 is a time vs. frequency plot of two waveforms for different embodiments of the test apparatus.

DETAILED DESCRIPTION OF THE INVENTION

The present invention provides a translation frame to increase the speed for survey use of an ultrasonic thermography apparatus in the analysis and inspection of the structural integrity of metal and composite structures. The preferred embodiment is particularly suitable for use with airplanes and is suitable for inspecting subassemblies and in-service airplanes for defects such as disbonds, delaminations, cracks, corrosion, embedded contaminants, inclusions, and voids. It should be understood, however, that the present invention is not limited in its use with aerostructures, being usable, for example, for the inspection and analysis of pipelines, railroad rolling stock, architectural and civil engineering construction, and other structures where human safety or costly failure is a concern.

Detailed description of the operation of the mechanism within the frame referenced herein is contained in patent application Ser. No. 10/324,014, Ultrasonic Thermography Inspection Method and Apparatus, filed Dec. 20, 2002, incorporated herein in its entirety by reference.

Figure 1:
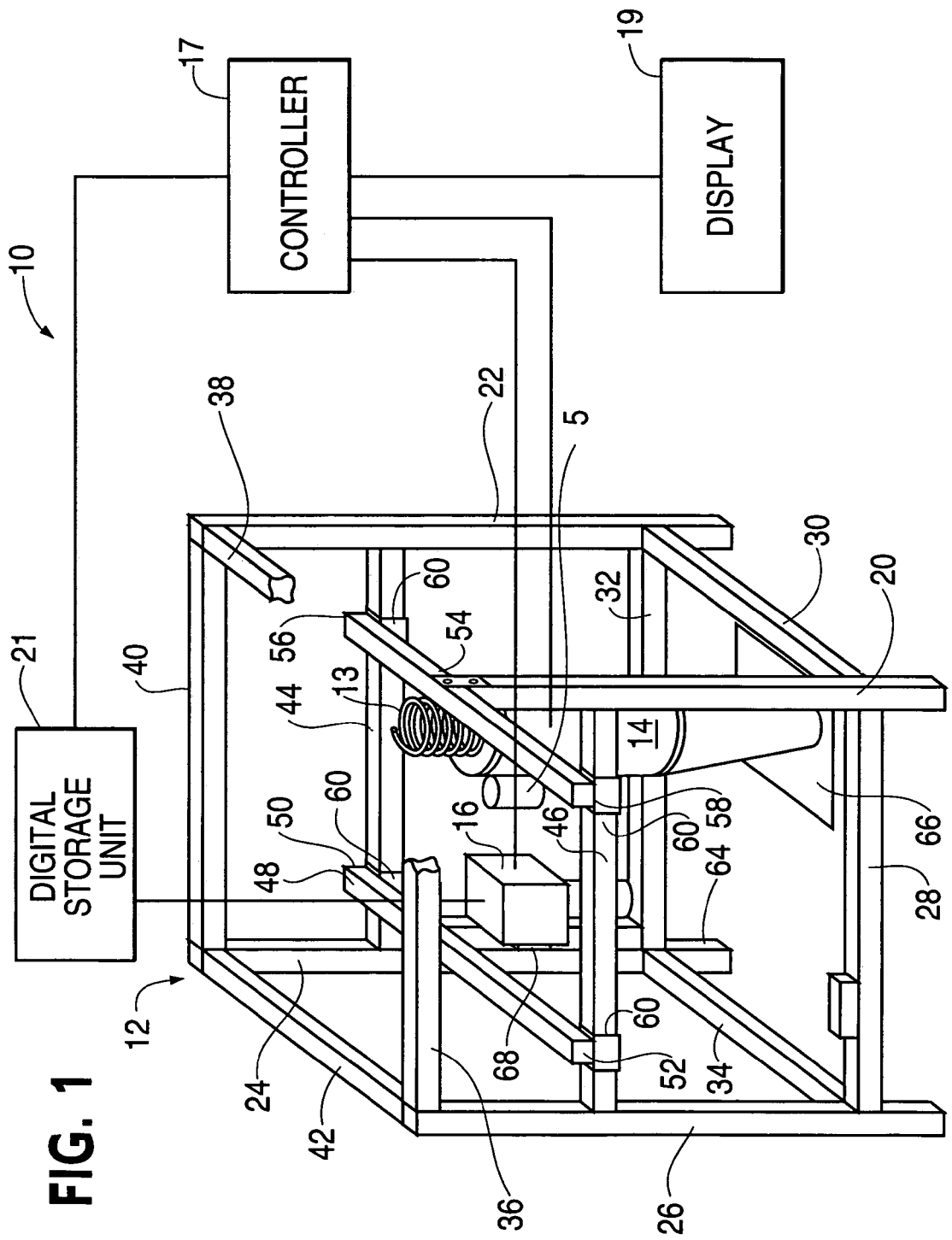
FIG. 1 is an illustration of an ultrasonic thermography inspection apparatus in accordance with a preferred embodiment of the present invention, showing a partially perspective view and a partially block diagram view.

Referring now to the figures, wherein like reference numerals indicate like elements, FIG. 1 shows a partial perspective view of an ultrasonic thermography inspection apparatus 10. The ultrasonic thermography inspection apparatus 10 includes a frame 12 having multiple frame members 20–54, a biasing element 13, a sound source, preferably an ultrasonic transducer 14 connected to an actuator 15, a thermal imaging camera 16, and a system controller 17. The apparatus 10 further includes a vacuum attachment assembly that includes four vacuum cups 108 (See FIG. 2) that are attached in the present inventive apparatus to the base framework 102. The system controller 17 can have an associated display 19.

As depicted in FIG. 1, the frame 12 preferably includes four vertical frame members 20; 22, 24 and 26 to which the vacuum cups 18a, 18b, 18c 18d are attached. The frame 12 additionally includes lower transverse frame members 28, 30, 32, 34. Lower transverse frame member 28 extends between and is attached to vertical frame members 26 and 20. Lower transverse frame member 30 extends between and is attached to vertical frame members 20 and 22. Lower transverse frame member 32 extends between and is attached to vertical frame members 22 and 24. And lower transverse frame member 34 extends between and is attached to vertical frame members 24 and 26. The frame 12 also includes upper transverse frame members 36, 38, 40, 42 that are coupled to and extend between the vertical frame members 20, 22, 24, 26. Upper transverse frame member 36 extends between and is attached to vertical frame members 20 and 26. Upper transverse frame member 38 extends between and is attached to vertical frame members 20 and 22. Upper transverse frame member 40 extends between and is attached to vertical frame members 22 and 24. Upper transverse frame member 42 extends between and is attached to vertical frame members 24 and 26.

The frame 12 of the apparatus 10 additionally includes a first cross bar 44 that is attached to and extends between vertical frame members 22 and 24 and a second cross bar 46 that is attached to and extends between vertical frame members 20 and 26. The frame 12 has a first slider bar 48 having a first end 50 slidably coupled to the first cross bar 44 and a second end 52 slidably coupled to the second cross bar 46 such that it can translate back and forth between vertical frame members 20, 22 and members 24, 26. The frame 12 also has a second slider bar 54 having a first end 56 slidably coupled to the first cross bar 44 and a second end 58 slidably coupled to the second cross bar 46 such that it can translate back and forth between vertical frame members 20, 22 and members 24, 26.

The slider bars 48, 54 are preferably coupled to the cross bars 44, 46 via linear bearings 60 or other suitable slidable coupling means known in the art that can enable it to slide along cross bars 44 and 46.

The actuator 15 is attached to a vertical holder bar 62 that is slidably coupled to the second slider bar 54. The vertical holder bar 62 is preferably rigidly attached to the holder bar 62 via mechanical attachment means such as bolt and/or clamp. Alternatively, the vertical holder may be coupled to the slider bar 54 via linear bearing or other suitable slidable coupling means known in the art such that it can translate between cross bars 44 and 46. Similarly, as depicted in FIG. 1, the thermal imaging camera 16 is adjustably mounted to the second vertical holder bar 68. The vertical holder bar 68 is rigidly attached to the holder bar 62 via mechanical attachment such as a bolt and/or clamp first slider bar 48. Alternatively, the vertical holder 68 may be coupled to the slider bar 48 via linear bearing or other suitable slideable coupling means known in the art such that it can translate between cross bars 44 and 46.

Figure 2:
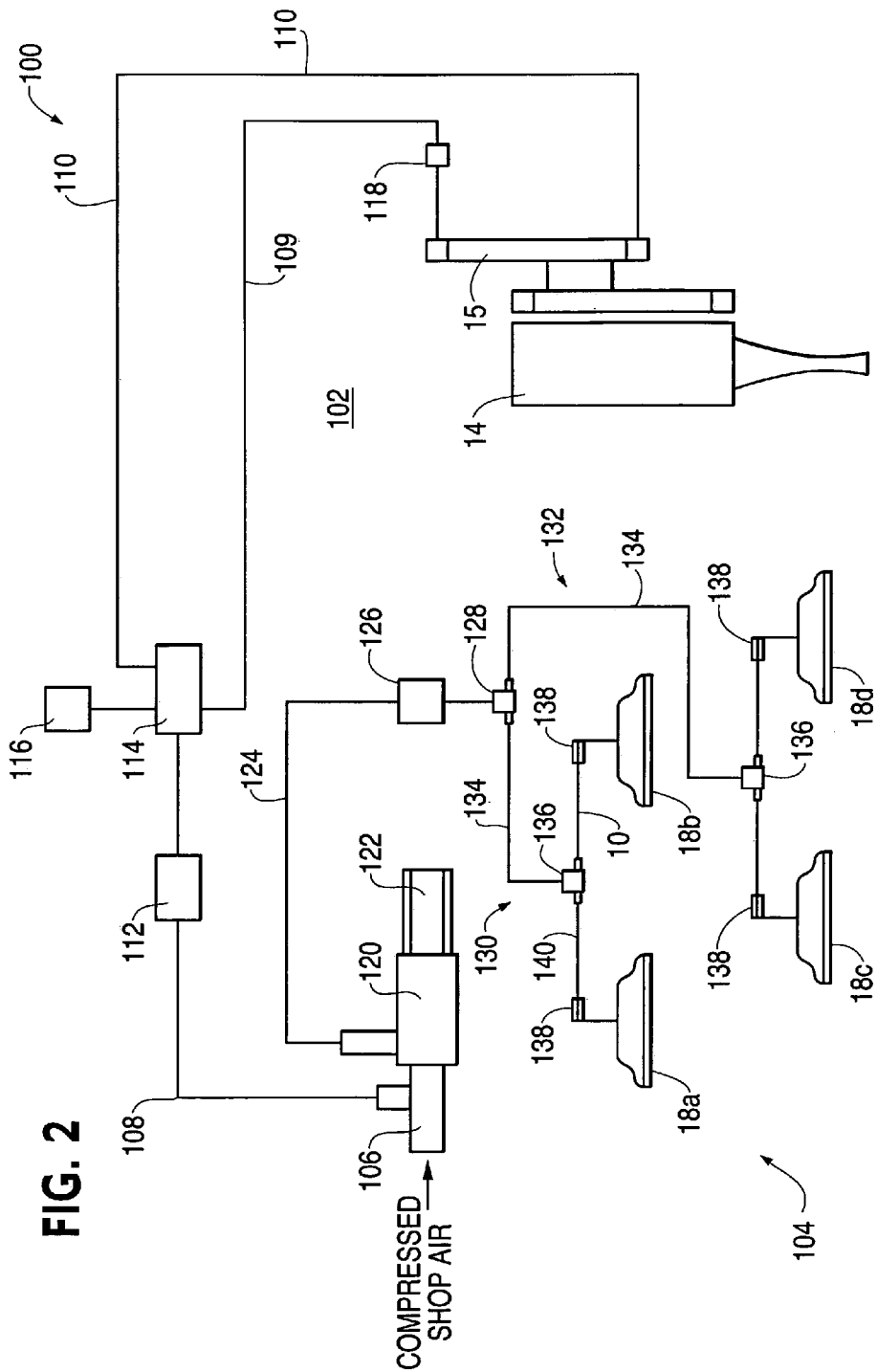
FIG. 2 is a schematic view of a pneumatic assembly utilized in a preferred embodiment of the present invention.

Referring now to FIGS. 1 and 2, the sound source 14 is preferably an ultrasonic transducer attached to the actuator 15. The transducer 14 preferably includes a piezoelectric element that generates ultrasonic energy within a desired ultrasonic or sonic frequency band for a certain length of time. The transducer 14 can be any transducer capable of generating ultrasonic energy preferably at varying ultrasonic frequencies, power levels and pulse durations. As depicted in FIG. 1, the biasing element 13 is preferably a spring that attaches to and extends between one of the upper frame members 36, 38, 40, 42 and the ultrasonic transducer 14. The spring 13 biases the transducer 14 in the downward direction or in the direction of the specimen to be analyzed. The spring 13 provides adjustable pre-load force between the ultrasonic transducer 14 and the specimen during attachment of the apparatus to the specimen. The pre-load force provided by the spring 13 is less than the suctioned force generated by the vacuum cups 18a, 18b, 18c, 18d allowing the transducer to translate in the upward direction or direction away from the specimen during attachment.

As depicted in FIG. 1, the ultrasonic energy from the transducer 14 can be coupled to a specimen, part or area to be tested through a coupler 66. The coupler 66 is a mechanical contact that is in contact with both the ultrasonic transducer 14 and the specimen. The coupler 66 is preferably a thin piece of soft metal, such as copper, that effectively couples the ultrasonic energy to the specimen. Alternatively, other materials known in the art other than copper may be used, for example, any material that is soft and malleable that can be deformed against the end of the transducer and prevent the transducer from bouncing and/or sliding along the specimen during operation. Alternatively, various applications, such as the analysis of composite materials, may not require the use of a coupler 66.

The actuator 15 is preferably a linear stroke, double action pneumatic actuator that functions to translate the ultrasonic transducer 14 in a generally upward and downward direction with respect to the specimen. The pneumatic actuator 15 can be powered by compressed air and can translate the ultrasonic transducer 14 such that the transducer 14 preferably applies approximately 10 lbs. to approximately 25 lbs. of force on the test surface or test specimen. More preferably, the actuator 15 exerts approximately 15 lbs. to approximately 20 lbs. of force. Use of the actuator 15 enables the analysis method herein described to be repeated and provides a consistent placement of the transducer 14 against the specimen and/or coupler 66.

The actuator 15 can be any actuator suitable for the purposes described herein. For example, actuation need not be pneumatic. While a representative pneumatic actuator may use an external air supply, a pressure regulator, and a fixed piston size to establish a fixed application force, an electrical actuator, driven by a motor and gear reducer, for example, can apply force, a strain gauge-based sensor can provide feedback, and a control circuit can regulate the applied force at the correct level.

Referring now to FIG. 2, a pneumatic assembly 100 employed in an embodiment of the present invention to power the pneumatic actuator 15 and vacuum cups 18a, 18b, 18c, 18d is schematically depicted. The assembly 100 is preferably a parallel system that includes the actuator system, generally designated 102, and an attachment assembly, generally designated 104. Each system, 102, 104 has a common compressed or pressured air inlet 106 where the pressurized air enters the pneumatic assembly 100.

As depicted in FIG. 2, the actuator system 102 has an air inlet conduit 108 for carrying pressurized air from the inlet 106 to the actuator system 102. The actuator system 102 further includes air conduits 109 and 110 which function to carry pressurized air to and from the actuator 15 during operation. The actuator system 102 also includes an air regulator 112, a controller 114, a first air control valve 116 and second air control valve 118.

The controller 114 is preferably a two position, four way spool valve that is toggle activated that controls the up and down movements of the actuator 15. Alternative controllers may also be utilized. When the controller 114 is in a first position, it pressurizes the air conduit 109 while it vents air conduit 110, causing the actuator 15 to translate the transducer 14 in the direction towards the specimen and contact the specimen. In this position, the first air control valve 116 functions to adjust the air pressure provided to the actuator 15, controlling the movement of the actuator 15 and transducer 14 toward the specimen. It also senses the pressure being exerted by the transducer 14 on the specimen and regulates the pressure being applied to specimen by the ultrasonic transducer 14.

Alternatively, when the controller 114 is in a second position, it pressurizes the air conduit 110 while it vents air conduit 109, causing the actuator 15 to translate the transducer 14 in the upward direction away from the specimen. In this position, the second air control valve 118 functions to adjust the air pressure provided to the actuator, controlling the movement of the actuator 15 and transducer 14 away from the specimen.

The air regulator 112, controller 114, first control valve 116 and second control valve 118 combine to control the amount of compressed air powering the actuator 15, in turn controlling the translation of the ultrasonic actuator 14, thereby controlling the distance at which the ultrasonic transducer 14 is positioned with respect to the specimen. In addition, the aforementioned components also combine to control the amount of pressure applied to the specimen by the transducer 14 via the actuator 15. The apparatus 10 is generally preferably arranged so that the actuator 15 moves the transducer 14 vertically downwards toward the specimen. However, other orientations are possible.

The preferred force level is a function of the properties of the ultrasonic transducer 14 and the physical properties of the expected test specimens. For typical transducers 14 capable of coupling power at levels on the order of a kilowatt at twenty kilohertz, and for typical aircraft production materials, for example, it has been demonstrated that twenty pounds of force is effective to fully couple the excitation into the specimen, both preventing the transducer 14 from lifting off during its stroke and allowing essentially full excursion of the transducer 14. Force levels significantly below about 10 pounds have been shown to allow the transducer 14 to lift free of the specimen, causing impacts that may damage the specimen and may produce anomalous out-of-band signal content. Force levels significantly above about 30 pounds tend to suppress the operation of the transducer 14, potentially preventing detection of significant defects.

It is to be understood from this discussion that the appropriate actuator 15 force level for various styles of transducers 14 may differ, and that some styles of ultrasonic transducers 14 may be better suited or entirely unsuited to apparatus of the type described herein. This may be determined by, among other issues, contact face size and the ability of the transducer 14 to maintain oscillation when coupled to the types of specimens for which the preferred embodiment is intended. It is to be further understood that testing of other materials, such as those that may be more highly internally damped, more massive, more brittle, or otherwise significantly different from typical aerostructures materials, may require different transducers 14 or different coupling pressures and methods for successful outcomes.

As illustrated in FIG. 2, the attachment assembly 104 is a vacuum attachment assembly having a venturi 120 coupled to the air inlet 106. The venturi 120 includes an exhaust muffler 122. The attachment assembly 104 also includes a vacuum conduit 124, a vacuum switch 126 and a two-way splitter 128 that splits the vacuum conduit 126 into two vacuum cup series, generally designated 130 and 132. Each of the series 130, 132 include two of the vacuum cups 18a, 18b, 18c, 18d. Alternative embodiments covered by the present invention may include more or less vacuum cups coupled to one another in multiple series or in a single series.

Each vacuum cup series 130, 132 includes a vacuum air conduit 134, a two-way splitter 136, a pair of check valves 138 and a pair of air conduits 140. The conduit 134 provides the vacuum suction to the two-way splitter 136 which splits the conduit and provides suction the assemblies' 130, 132 and their respective vacuum cups via the conduits 140 and the check valves 138. The check valves 138 allow vacuum air to be provided to individual vacuum cups 18a, 18b, 18c, 18d or removed from individual vacuum cups 18a, 18b, 18c, 18d whereas the switch 126 functions to turn the vacuum air "on" or "off" in the entire attachment assembly 104.

During operation, compressed air from the inlet 106 enters the venturi 120 and exits the exhaust 122, creating a vacuum. When the vacuum switch 126 is in the "on" position, vacuum air is provided to the vacuum cups 18a, 18b, 18c, 18d via the above described conduits, splitters and check valve components, enabling the apparatus 10 to be attached to the specimen, part and/or component to be analyzed. Alternatively, when the vacuum switch 126 is in the "off" position, vacuum air is not provided to the vacuum cups 18a, 18b, 18c, 18d and the apparatus cannot be attached to the specimen, etc.

As illustrated in FIG. 1, the thermal imaging camera 16 is preferably an infrared camera that generates images of the specimen, part or area being tested in association with ultrasonic excitations of the test specimen, part or area. In addition, the infrared camera 16 can convert the heat energy detected to grayscale information if desired. The images and grayscale information are preferably displayed on the image display 19. The image information is captured preferably by using a digital storage unit 21, located within the apparatus 10 or located remotely and accessed electronically. Preferably, digital storage unit 21 allows for the infrared images to be recorded digitally and/or by standard video, depending upon application and the size of the defect.

Alternatively, the image data and grayscale data may stored in databases located within the ultrasonic thermography inspection apparatus 10, located within storage media or located remotely. The remotely located databases can be accessible by corded and/or wireless communication including the Internet, Ethernet, or other remote memory storage facility. The storage media upon which the image and grayscale information is stored can include, but is not limited to, floppy disc (including ZIP); tape drive cartridge (such as DAT); optical media (such as CD-ROM, DVD-ROM, etc.); flash memory (such as smart media, compact flash, PC card memory, memory sticks, flash SIMMs and DIMMS, etc.); magnetic based media, magneto optical; USB drives; Nanotechnology memory or any other storage media that an operator can store or retrieve information from it. A person skilled in the art will recognize that any suitable storage media can be used.

As previously described, the infrared camera 16 is mounted to the vertical holder bar 64 that extends from the slider bar 48. The infrared camera 16 is preferably mounted to the vertical holder bar 64 via linear bearing or other suitable coupling means known in the art such that the camera 16, enabling it to be positioned at varying distances from the specimen, test part or area. The aforementioned positioning of the infrared camera allows the camera 16 to move along a X, Y and Z axis, allowing the camera to be positioned at multiple locations with respect to the part or area being tested.

The system controller 17 may be disposed within the frame 12 where it directly communicates with the ultrasonic transducer 14 and thermal imaging camera 16 via wires. The system controller 17 can be any computer suitable for carrying out the analysis process described herein. Alternatively, the controller 17, may be remotely located away from the apparatus 10 and communicate in either a corded or wireless fashion with the camera 16 and ultrasonic transducer 14. Similarly, the image and grayscale data may be stored locally on the unit on a hard drive, compact disc, other storage media or may be stored remotely via corded or wireless communication.

During operation, analysis and/or inspection is initiated by first attaching the ultrasonic thermography apparatus 10 to the specimen to be analyzed by switching the previously described vacuum switch 126 "on," activating the attachment apparatus 104. Next, a baseline image of the test area is taken by the infrared camera 16 and stored in the digital storage unit 21 or other storage media previously described, providing a reference point for analysis. The ultrasonic transducer 14 is then positioned and adjusted such that it is held in contact with the test surface using the pneumatic actuator 15 and controller 114, providing proper pressure between the specimen and/or coupler 66 and the transducer 14.

Also during operation, the system controller 17 provides timing between the transducer 14 and the infrared camera 16. Once the analysis process is initiated, the controller 17 causes the camera 16 to begin taking sequential images of the specimen, test part or area at a predetermined rate. Once the image sequence begins, the controller 17 sends a signal to the transducer 14 to generate the ultrasonic signal. The ultrasonic energy is in the form of a pulse at a predetermined frequency. The pulse time periods and frequencies and input power of the apparatus 10 can vary depending on the apparatus being used and the composition of the area or part being tested.

Upon application of the ultrasonic energy, the specimen becomes "excited" and the areas of the test area that contain defects vibrate with greater amplitude and cause the surface to heat up, which is detected by the camera 16 and can be viewed on the display and/or stored. The camera 16 may also convert the heat energy images is to grayscale information. The grayscale information is then sent to the display and/or stored for later review and analysis. If the grayscale level of the test area during the application of ultrasonic energy exceeds the baseline threshold level previously recorded, the peak store image capture unit records and retains this new level on the image display, immediately notifying the operator of the existence of defects. The above-described process may now be repeated on the same area or the apparatus may be transferred to a new area to be tested.

Figure 3:
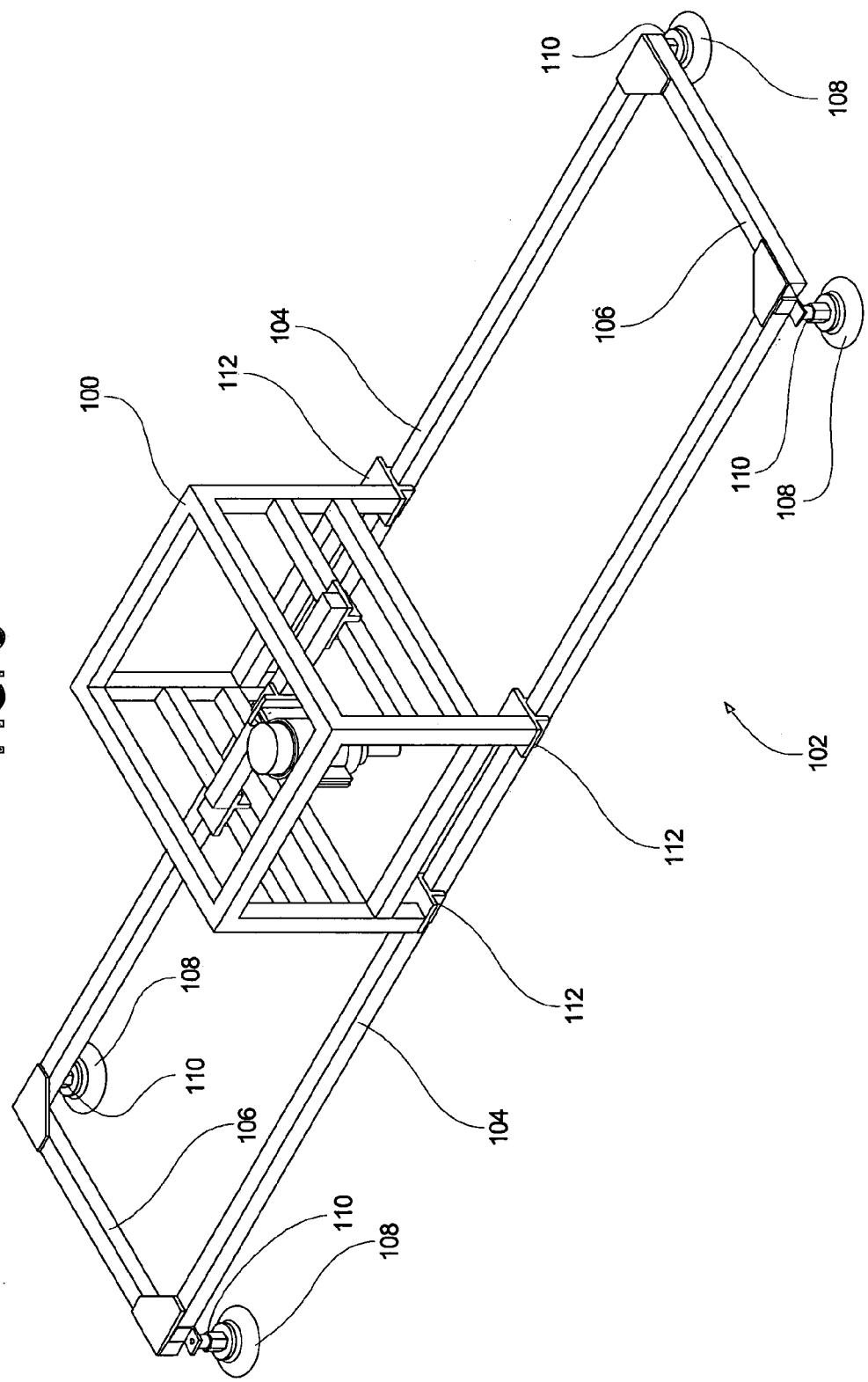
FIG. 3 is an oblique view of a preferred embodiment of the present invention, incorporating the apparatus of FIG. 1 and resting on a novel base that permits x-axis translation.

FIG. 3 illustrates a frame 100 equivalent to that of FIG. 1 carried on a base 102, the latter comprising longitudinal guide rails 104 and cross members 106. FIG. 2 further shows vacuum cups 108 located on adjustable legs 110 on the base 102, where the vacuum cups 108 can attach to a test specimen, while the interface between the frame 100 and the base 102 can be comprised of low-friction sliding fittings 112, such as linear bearings sized and configured to move smoothly along the longitudinal guide rails 104. A clamp, such as those integral with each of the sliding fittings 112 in the exemplary embodiment, can be actuated to hold the frame at any preferred location along the longitudinal guide rails 104.

Figure 4:
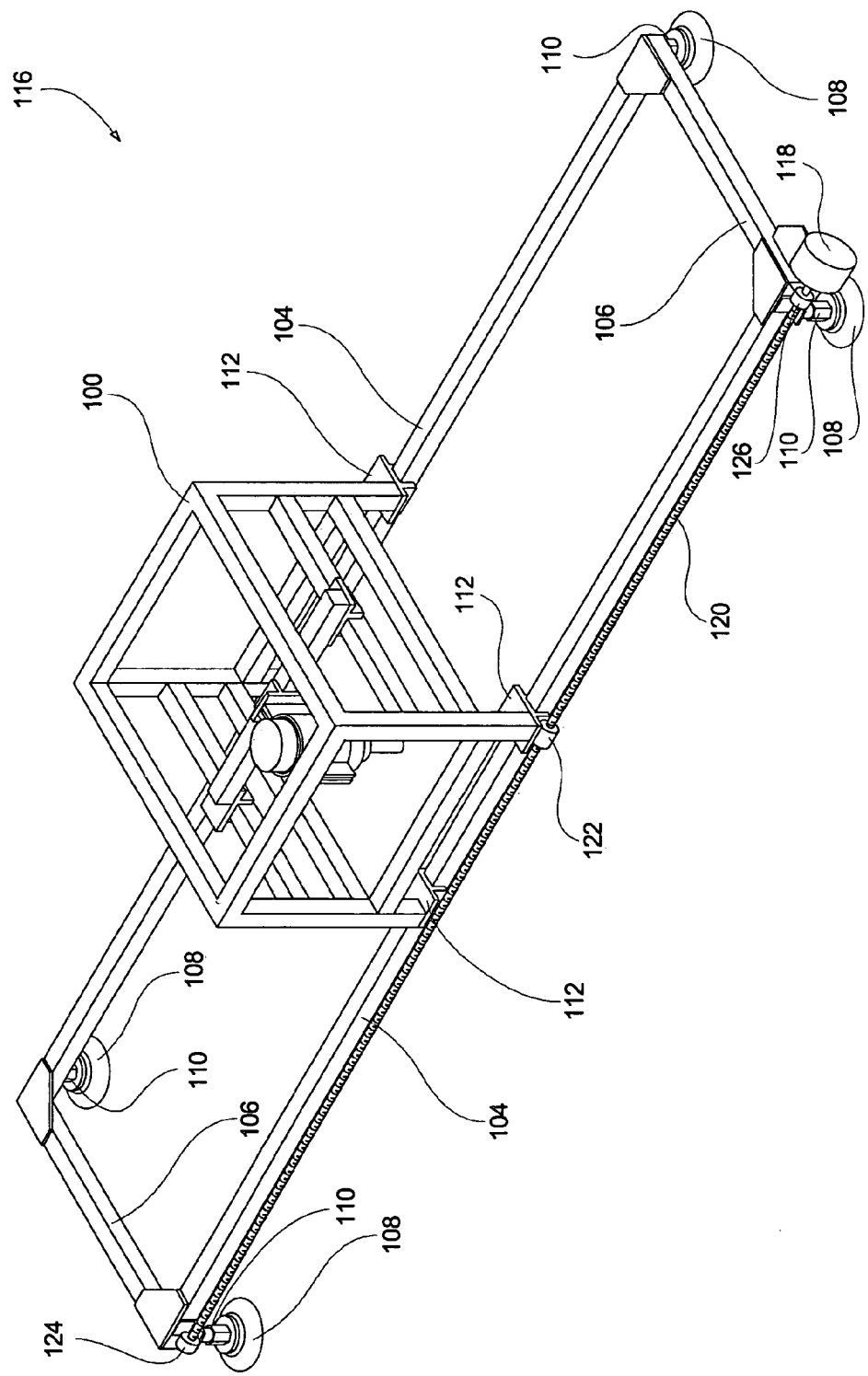
FIG. 4 is an oblique view of a motorized version of the manually positioned apparatus of FIG. 2.

FIG. 4 illustrates an apparatus 116 similar to that of FIG. 3, but with a positioning motor 118 to provide torque, a drive screw 120 to translate torque to linear force, a ball nut 122 to couple the linear force to the frame, an end bearing 124 to contain the drive screw 120, and a turns counter 126 to sense position in turns of the drive screw 120. This configuration permits a single operator to command the apparatus 116 to reposition the test frame 128 remotely, while remaining at a viewing console throughout a series of test operations. Positioning motor 118 design may be such as to hold the frame 100 in place when deenergized, to use the reduction ratio in an integral or external gearbox (not shown) to perform the holding function, to use an external braking device similar to that of the apparatus of FIG. 3, or an equivalent function to permit the frame 100 to remain fixed during a test event for any orientation of the base 102. Other positive positioning technologies include chain and rack-and-pinion drives.

Contemporary applications for the apparatus call for controlled positioning along a single axis perpendicular to the head pressurization axis, with the third perpendicular axis fixed. This allows a lightweight system to be assembled that permits several tests to be performed between repositionings of the apparatus. An apparatus that can be positioned or can position itself over both of the axes perpendicular to the head pressurization axis may be of use in examining large, nearly flat surfaces such as aircraft wings, architectural construction panels, and the like. Such an apparatus has a second base framework interposed between the head assembly and the vacuum pads, with guide rails perpendicular to those of the guide rails of a single-axis apparatus.

It is to be understood that the spatial orientation of the exemplary apparatus described herein may be any orientation without significant effect on function. For example, in performing examination of an aircraft fuselage, the exemplary apparatus may be attached to the top, the bottom, and all other possible regions of the subject fuselage, with the transducer pointed generally toward the central axis of the fuselage. Thus the actuator 15 mechanism will press the transducer 14 downward in some orientations, upward in others, and at any intermediate angle in some application. It has been shown that the low mass of an exemplary ultrasonic transducer 14 and the high retention force of a multiplicity of vacuum cups 108 allow an actuator 15 to provide a substantially invariant force level at all orientations of the exemplary apparatus, affording relatively uniform imaging performance.

For applications such as pipelines, a configuration with straight guide rails as shown herein in the flow direction and curved guide rails in the circumferential direction may be appropriate if for example many lengths of pipe of a single diameter are to be examined. For such an application, helical frame advancement may be preferable, as may a self-contained power system and wireless communication.

Similarly, positioning by systems other than a linear guide frame adhered to the test object with vacuum pads may be preferable, including, for example, polar instead of rectangular coordinate positioning (i.e., r-θ instead of x-y), and multiple-degree-of-freedom robotic arm positioning with the transducer/imager assembly serving as the so-called end effector of the robotic arm.

FIG. 5 shows a constant-frequency waveform 150 and a swept-frequency waveform 152 for two embodiments of the preferred apparatus. The constant-frequency waveform 150 is relatively straightforward to generate at the high signal level desirable for the preferred apparatus and reasonably effective for detection. The waveform 150 may be realized using, for example, a quartz crystal of appropriate dimensions, excited by an electronic drive circuit at its working frequency. The swept-frequency waveform 152 is readily produced at low power levels, although it remains comparatively costly at high power levels at the current state of the technology for ultrasonic transducers.

The swept-frequency transducer has the advantage of providing in the test subject excitation of defects that resonate at many frequencies, the effect of which is to cause appreciable increase in the induced motion within defects of many sizes of interest. The rapid heating of defects caused by this phenomenon may increase detection speed or likelihood, particularly at greater depths, where detection is otherwise less assured. As an alternative to a swept frequency transducer, a multiplicity of transducers can be used that interoperate to excite at multiple frequencies over a range, so that the resonant frequencies of defects of many sizes are approximated, with an effect that may be intermediate between that of a single-frequency transducer and that of a swept frequency transducer.

The many features and advantages of the invention are apparent from the detailed specification, and, thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and, accordingly, all suitable modifications and equivalents may be resorted to that fall within the scope of the invention.

What is claimed is:

1. A portable thermal imaging analysis apparatus for analyzing a specimen having a surface, comprising:
    a base framework that removably attaches to the specimen;
    a plurality of vacuum cups that can be selectably activated to removably attach said base framework to the specimen;
    a frame that slideably attaches to said base framework;
    a sound source that mounts to said frame and couples its energy to the specimen;
    a thermal imaging camera directed toward the specimen; and
    a controller connected to said sound source and said thermal imaging camera.

2. The portable thermal imaging analysis apparatus according to claim 1, wherein said frame is mounted to said base framework via at least one first sliding fitting mounted to said frame, whereby said frame translates along an axis generally parallel to the surface of the specimen.

3. The portable thermal imaging analysis apparatus according to claim 2, wherein said sliding fitting comprises a linear bearing.

4. The portable thermal imaging analysis apparatus according to claim 1, wherein said base framework further comprises at least one first guide rail.

5. The portable thermal imaging analysis apparatus according to claim 4, wherein said first guide rail comprises a structural extrusion.

6. The portable thermal imaging analysis apparatus according to claim 1, wherein said vacuum cups are pivotably attached to said base framework.

7. The portable thermal imaging analysis apparatus according to claim 4, wherein said base framework further comprises:
    a cross rail perpendicular to said first guide rail and roughly parallel to the specimen surface; and
    a second sliding fitting slideably connecting said first guide rail to said cross rail.

8. A portable thermal imaging analysis apparatus for analyzing a specimen having a surface, comprising:
    linear-stroke-piston means for generating an acoustic signal characterized by a principal frequency that changes with time;
    means for removably attaching said generating means to a specimen;
    means for moving said generating means across a region of the surface of the specimen;
    means for detecting transient thermal response to stimulation by said generating means; and
    means for controlling said generating means and said detecting means.

9. The portable thermal imaging analysis apparatus according to claim 8, wherein said moving means further comprises means for minimizing frictional drag in the moving of said generating means across the region of the surface of the specimen.

10. The portable thermal imaging analysis apparatus according to claim 8, wherein said moving means further comprises:
    means for releaseably locking said moving means in a position.

11. The portable thermal imaging analysis apparatus according to claim 8, wherein said attaching means further comprises means for pressureably coupling said moving means to the surface of the specimen.

12. The portable thermal imaging analysis apparatus according to claim 8, wherein said detecting means further comprises:
    means for storing an image acquired by said detecting means;
    means for displaying an image acquired by said detecting means; and
    means for joining into a single composite image a plurality of images acquired by said detecting means.

13. A method for portable thermal imaging analysis of a specimen having a surface, comprising the steps of:
    attaching a thermal imaging apparatus to a specimen;
    repositioning said thermal imaging apparatus at a multiplicity of sites across a region of a specimen, comprising:
        activating a drive mechanism to advance said thermal imaging apparatus along a guide rail,
        monitoring position until a destination position has been reached, and
        deactivating the drive mechanism;
    generating an acoustic signal with energy content along a motional axis generally perpendicular to a surface of a specimen;
    detecting thermal response to stimulation by the acoustic signal; and
    controlling the acoustical signal generation and image detection operations.

14. The method for portable thermal imaging analysis according to claim 13, wherein said repositioning step further comprises:
    releasing a motion preventing clamp;
    moving the thermal imaging apparatus along a guide rail;
    positioning the thermal imaging apparatus according to a positioning indicator; and
    reapplying the motion preventing clamp.

15. The method for portable thermal imaging analysis according to claim 13, wherein said repositioning step further comprises:
    receiving a command from a control apparatus to advance the thermal imaging apparatus;
    overcoming a motion preventer mechanism;
    reenabling the motion preventer mechanism; and
    transmitting a response to the control apparatus that repositioning is complete.

16. A portable thermal imaging analysis apparatus for analyzing a specimen having a surface, comprising:
    a frame that removably attaches to the specimen;
    a sound source that mounts to said frame and couples acoustical energy into the specimen, the sound source comprising a linear stroke piston that oscillates at a varying rate, wherein the acoustical energy is characterized by a principal frequency that changes with time;
    a thermal imaging camera that captures infrared images of the specimen; and
    a controller connected to said sound source and said thermal imaging camera.

17. The portable thermal imaging analysis apparatus according to claim 16, wherein said sound source further oscillates under the control of a control apparatus.

18. The portable thermal imaging analysis apparatus according to claim 16, wherein said sound source oscillates at an increasing rate during an activation period.

19. The portable thermal imaging analysis apparatus according to claim 16, wherein said sound source oscillates at a frequency that increases as a logarithmic function of time during an activation period.

20. The portable thermal imaging analysis apparatus according to claim 16, wherein said sound source oscillates at a frequency that varies over a range of an octave.

21. The portable thermal imaging analysis apparatus according to claim 16, wherein said sound source oscillates at a frequency that varies over a range of a decade.

22. The portable thermal imaging analysis apparatus according to claim 16, wherein said sound source emits an output signal that is comprised of a plurality of frequencies simultaneously.

23. The portable thermal imaging analysis apparatus according to claim 16, wherein said sound source emits an output signal that is comprised of a plurality of frequencies emitted sequentially.

24. The portable thermal imaging analysis apparatus according to claim 16, wherein said sound source emits an output signal that is comprised of a fundamental frequency and a plurality of harmonics thereof.

25. The portable thermal imaging analysis apparatus according to claim 16, wherein said sound source emits an output signal comprising:
   a fundamental frequency summed with a carrier frequency; and
   a plurality of additional frequencies, each of which comprises a harmonic of the fundamental frequency summed with the same carrier frequency.

26. The portable thermal imaging analysis apparatus according to claim 16, wherein said sound source emits an output signal that is comprised of a mixture of frequencies distributed over a range.

27. The portable thermal imaging analysis apparatus according to claim 1, wherein said specimen is at least a portion of one selected from the following aircraft subassemblies: a section of an aircraft fuselage, an aircraft wing, and an aircraft structural component.

28. The portable thermal imaging analysis apparatus according to claim 1, wherein said specimen is at least a portion of an in-service airplane.

29. The portable thermal imaging analysis apparatus according to claim 8, wherein said specimen is at least a portion of one selected from the following aircraft subassemblies: a section of an aircraft fuselage, an aircraft wing, and an aircraft structural component.

30. The method for portable thermal imaging analysis according to claim 13, wherein said specimen is at least a portion of one selected from the following aircraft subassemblies: a section of an aircraft fuselage, an aircraft wing, and an aircraft structural component.

31. The portable thermal imaging analysis apparatus according to claim 16, wherein the specimen is at least a portion of one selected from the following aircraft subassemblies: a section of an aircraft fuselage, an aircraft wing, and an aircraft structural component.

* * * * *